US009578873B2

(12) United States Patent
Folgarait et al.

(10) Patent No.: US 9,578,873 B2
(45) Date of Patent: Feb. 28, 2017

(54) METHODS FOR CONTROLLING LEAF-CUTTING ANTS

(71) Applicant: UNIVERSIDAD NACIONAL DE QUILMES, Bernal-Prov. de Buenos Aires (AR)

(72) Inventors: Patricia Folgarait, Bernal (AR); Daniela Goffre, Bernal (AR); Jorge Ariel Marfetan, Bernal (AR)

(73) Assignee: UNIVERSIDAD NACIONAL DE QUILMES, Bernal, Prov. de Buenas Aires (AR)

( * ) Notice: Subject to any disclaimer, the term of this patent is extended or adjusted under 35 U.S.C. 154(b) by 0 days.

(21) Appl. No.: 14/351,041

(22) PCT Filed: Oct. 10, 2012

(86) PCT No.: PCT/IB2012/055484
§ 371 (c)(1),
(2) Date: Apr. 10, 2014

(87) PCT Pub. No.: WO2013/054272
PCT Pub. Date: Apr. 18, 2013

(65) Prior Publication Data
US 2014/0322339 A1    Oct. 30, 2014

Related U.S. Application Data

(60) Provisional application No. 61/545,792, filed on Oct. 11, 2011.

(51) Int. Cl.
*A01N 25/00* (2006.01)
*A01N 63/04* (2006.01)

(52) U.S. Cl.
CPC ........... *A01N 25/006* (2013.01); *A01N 63/04* (2013.01)

(58) Field of Classification Search
None
See application file for complete search history.

(56) References Cited

U.S. PATENT DOCUMENTS

| 6,344,208 | B1 * | 2/2002 | Howse | A01M 1/20 424/405 |
| 6,403,085 | B1 | 6/2002 | Stimac | |
| 7,951,389 | B2 | 5/2011 | Stamets | |
| 2002/0124458 | A1 * | 9/2002 | Clark | A01M 1/026 43/124 |
| 2002/0146394 | A1 * | 10/2002 | Stamets | A01N 63/04 424/93.5 |

FOREIGN PATENT DOCUMENTS

| EP | 2578222 | * | 10/2013 | ............. A61K 36/53 |
| GB | 1516099 | | 6/1978 | |
| WO | 9011012 A1 | | 10/1990 | |
| WO | 9102051 A1 | | 2/1991 | |
| WO | 9424871 A1 | | 11/1994 | |
| WO | 9525430 A1 | | 9/1995 | |
| WO | 9618722 A2 | | 6/1996 | |
| WO | 9716974 A1 | | 5/1997 | |
| WO | 0228189 A2 | | 4/2002 | |
| WO | 2004052103 A1 | | 6/2004 | |
| WO | 2006121350 A1 | | 11/2006 | |

OTHER PUBLICATIONS

Calle et al. Leaf-cutting ants revisited: Towards rational management and control, Int. J. Pest Management, 2012, vol. 58, pp. 235.*
Alves et al. in insecticide-development of safer and more effective technology, Ed. Trdan, InTech, 2013, Croatis, Chapter 9, Plant derived products for leaf-cutting ants control, p. 264.*
Varon (Distribution and foraging by the leaf-cutting ant, *Atta cephalotes* L., in coffee plantations with different types of management and landscape contexts, and alternatives to insecticides for its control, 2006, Thesis, chapter 5, Effect of baits based on fungal strains or botanical extracts on Atta cephalotes colonies).*
Mercahnt (Texas Leaf cutting ants, Insects in the City, 2015, pp. 1-5, http://citybugs.tamu.edu/factsheets/landscape/ants/ent-1002/).*
Currie (Prevalence and impact of virulent parasite on a tripartite mutualism, Oecologia, 2001, vol. 128, p. 99-106).*
Lopez et al. (Matrhizium anisopliae and Trichoderma virde for control of nests of the fungus-growing ant, *Atta cephalotes*, Biological Contrl. 2003, vol. 27, pp. 194-200).*
Terezinha M.C. Della Lucia, "As Formigas Cortadeiras", 1993, Chapters 1 and 8, pp. 1-3,84-105.
Mark S. Goettel, et al. "Chapter V-3 Fungi: Hyphomycetes",1997, pp. 213-249. Lawrence Lacey, "Manual of Techniques Insect Pathology".
J.J. Knapp, et al. "Factors Controlling Foraging Patterns in the Leaf-Cutting Ant *Acromyrmex octospinosus*", 1990, pp. 382-409.
Bert Holldobler, et al. "The Ants", 1990, Chapter 17, pp. 596-608.

\* cited by examiner

*Primary Examiner* — Bethany Barham
*Assistant Examiner* — Ping Cao
(74) *Attorney, Agent, or Firm* — Nath, Goldberg & Meyer; Joshua B. Goldberg; Tanya E. Harkins

(57) ABSTRACT

Kits for biological control of leaf-cutting ants are disclosed. The kits comprise at least two granulated bait formulations, each formulation containing a) a biologic control agent for the ants, and b) one masking substance for the control agent and/or one attractant, wherein the control agent is the same in all formulations, and wherein the masking substance and/or attractant are different in each formulation.

14 Claims, 15 Drawing Sheets

METHODS FOR CONTROLLING LEAF-CUTTING ANTS

The present invention relates to methods and compositions for controlling leaf-cutting ants. More particularly, the present invention relates to methods and kits for controlling leaf-cutting ants by serially supplying different formulations, and to a method for producing conidia of *Escovopsis* fungus useful as controlling agent in the methods and compositions of the present invention.

BACKGROUND

Among social insects, ants constitute one of the main pests that adversely affect human activities. For instance, leaf-cutting ants of the genera *Atta* and *Acromyrmex* (Order Hymenoptera, Family Formicidae, Subfamily Myrmecinae, Tribe upper Attini) are endemic of the Neotropics. These ants cut pieces of fresh plant matter (leaves, flowers, fruits), which are then transported to the ant nests and used as substrate for growing of the symbiotic *Leucoagaricus* fungus that these ants use as their main source of food. Leaf-cutting ants are the main herbivores of the Neotropics, and their impact in agriculture has been estimated in billions of US dollars every year, both by directly attacking crops and plantations and by competing for pastures with livestock (Robinson S. W. and H. G. Fowler (1982). Foraging and pest potencial of paraguayan grass-cutting ants (*Atta* and *Acromyrmex*) to the cattle industry. Z. Angew. Ent 93: 42-54; Hölldobler, B. and Wilson, E. O. (1990) *The ants*, Harvard University Press. Cambridge, Mass., USA; Della Lucia T. M. C. (ed.) (1993). As formigas cortadeiras. Bib. Cent. Univ. Fed. Viçosa Brasil.). Beyond the economic loss infringed every year for its damage to plantations of native and exotic species, to crops of citrus, yerba mate, and vegetables, people perceives them negatively because they destroy ornamental plants in the gardens.

Combat of social insects, as ants, presents challenges that are different from controlling solitary organisms. For instance, there is a difference in the concentration of individuals of the pest species (a single organism versus thousands to millions of individuals in a colony). Furthermore, in social insects the queen is the only colony member that reproduces, and is very well protected. As an example, in leaf-cutting ants the queen is the first one to escape in case of danger, carrying with her a piece of the *Leucoagaricus* fungus that these ants use as source of food and founding a new colony at a different site.

The fact that leaf-cutting ant colonies build their nest well protected underground makes it difficult under usual conditions to directly apply poisons or pesticides which could result in an effective control of the whole colony. With this in mind, the more efficient control is achieved by insufflating a controlling agent through every entrance/exit of the nest. However, this procedure is labor-consuming and requires the use of special equipment, which raises costs, and even then it can be ineffective as the controlling agent might not reach the queen due to the large underground dimensions and the numerous chambers that a giant nest may have. For countering this problem, advantage has been taken of the characteristic behavior of the leaf-cutting ants of carrying pieces of leaves to the nest interior by using baits impregnated with pesticides of long-lasting residual effect, which are carried by the ants to places otherwise inaccessible within the nest, thus affecting the health of the colony in a more efficient way. Nevertheless, social insects, and especially leaf-cutting ants, also present complex cleaning behavior. Leaf-cutting ants can learn to recognize a particular food item, and as a result come back for more or reject it (Knapp J, Howse P. E y A. Kemarrec. 1990. Factors controlling foraging patterns in the leaf-cutting ant *Acromyrmex octospinosus*. In *Applied Myrmecology: a world perspective*, Eds. R. K. Vander Meer and K. Jaffé, pp 382-409, Boulder, Colo.: Westview Press; Herz H, Hölldobler B and F. Roces. 2008. *Delayed rejection in a leaf-cutting ant after foraging on plants unsuitable for the symbiotic fungus*. Behavioral Ecology 19: 575-582; Saverscheck N, Herz H, Wagner N y F. Roces. 2010. *Avoiding plants unsuitable for the symbiotic fungus: learning and long-term memory in leaf-cutting ants*. Animal Behaviour 79: 689-698). Regarding rejection, workers can inspect a food source and leave it without carrying it, they can start to eat or carry it just for leaving abandoned afterwards, they can carry the resource to the nest but reject it at subsequent times, or they can carry a same resource to the nest several times but at a decreasing rate in time. It has been also demonstrated that these ants can associate. Thus, leaves usually attractive for the ants, impregnated in a fungicide which affects the *Leucoagaricus* gardens may be carried to the nest at first, but then will appear in the colony's refuse dump, as these leaves are removed from the fungus growing chamber. Moreover, when baits infected with a mycopathogenic fungus are accepted, the ants later reject the same bait, even if it is not infected with the pathogen. This memory-associated rejection can start 24-48 hours after the damaging resource is offered and last from 18-30 weeks. Because the effective control of a pest often requires repeated exposure of the target organism to the controlling agent, the delayed rejection mechanism displayed by leaf-cutting ants reduces the efficiency of using baits for fighting them (Ridley P, Howse P. E. and C. W. Jackson. 1996. *Control of the behavior of leaf-cutting ants by their symbiotic fungus*. Experientia 52: 631-635).

Traditionally, social insect's pest control has relied upon the use of chemical pesticides. Several well-known problems are associated to the use of pesticides, such as negative impact on human health, persistence in the ecosystem, and lack of specificity, incidentally adversely affecting many non-damaging organisms, including those which could be beneficial for combating the very same pest whose control is desired. The use of many pesticides of common use in the past has been banned by local authorities around the world for the risk that they pose to the people and the environment, and many other became ineffective as pest populations developed resistance and became immune to them. Moreover, chemical control of ants is highly inefficient since the queen is seldom adversely affected and then the colony being fought can relocate to a nearby location.

An alternative to the use of pesticides is biological control of pests. Biological control, or biocotrol, utilizes the natural enemies of the pest for controlling its populations. For instance, fungi which are insect pathogens have been used for controlling unwanted insects, as disclosed in Patent Applications WO9102051, WO9424871 WO9525430, WO0228189, WO2006121350 y WO2004052103, and in U.S. Pat. No. 7,951,389 y U.S. Pat. No. 6,403,085. Use of fungi which are pathogens of other fungi is discussed in WO016974 y WO9618722A2, which use strains of *Trichoderma* for combating phytopathogenic fungi, and there is even a commercial product (Attacebo) which uses *Trichoderma* for destroying the *Leucoagaricus* gardens grown by leaf-cutting ants. However, biological control usually requires repeated exposure of the target organism to its pathogen, and the delayed rejection mechanism makes the use of baits as carriers in methods of biological control of leaf-cutting ants particularly inadequate because their memory and associative ability.

From the foregoing it is clear that new methods for fighting leaf-cutting ants are needed which eliminate them in spite of the protection provided by ant nests. In particular, methods for fighting leaf-cutting ants by using baits are needed whose efficiency is not hindered by the delayed rejection mechanism.

BRIEF SUMMARY

The aforementioned problems are solved according to the present invention by a method for controlling leaf-cutting ants which comprises serially supplying at least two different bait formulations, where each formulation comprises at least one ant controlling agent. Since association and learning in leaf-cutting ants is performed mainly by means of the olfactory system, each formulation used in the various steps also contains a different attractant and/or controlling agent masking substance, so the ants identify it as a different formulation than the one provided before. Additionally, the formulations may differ also on its consistence, texture, odor, color, germination medium or other features, which constitute additional barriers for the association of the formulations with the controlling agents and subsequent learning by the ants.

According to a particular embodiment, the method of the invention comprises performing a single cycle of applying the bait formulations. In an alternative embodiment, when required by the ant species and the size of the colony, the method of the invention comprises more than one cycle of applying the bait formulations.

The controlling agent can be a chemical pesticide affecting the ants in a direct manner or by killing their food source (i.e. fungicides). The controlling agent can be also a plant extract, in the form of essential oils or secondary compounds or other made by plants, which present insecticide or fungicide action. The controlling agent can also be a pathogen affecting ants in a direct way, or affecting ants in an indirect way by damaging or even killing the *Leucoagaricus* fungus that the ants use as food supply.

According to another aspect of the present invention, kits for the biological control of leaf-cutting ants according to the method of the present invention are provided. The kits of the invention comprise at least two bait formulations containing at least one controlling agent for the ants and differing among them in the attractant and/or controlling agent masking substance, and optionally in at least one feature selected from consistence, texture, germination medium, grain size, and color. The formulations that are part of the kit of the invention can be in the form of dry pellets or as gelatinous granulated formulations, and beyond an attractant they can comprise conidia germination media.

According to another aspect of this invention, a method for inducing production of *Escovopsis* conidia useful as controlling agent of the method of the invention is provided, in which conidiated and non-conidiated *Leucoagaricus* fungus micelia, or fragments (free of micelia) of the growing medium of *Leucoagaricus* cultures are added to the *Escovopsis* culture medium.

DETAILED DESCRIPTION

Figure 1:
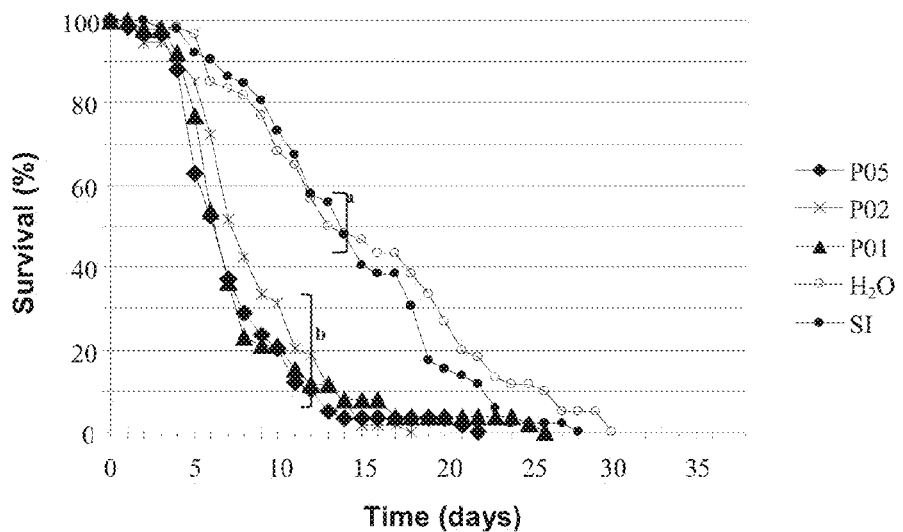
FIG. 1 shows survival according to the Kaplan-Meier's method of ants treated with three isolates of *Purpureocillium lilacinum* P01, P02 y P05, with water ($H_2O$) y and without inmmersion (S/I) as described on Example 3. Different letters imply significant differences between survival distributions for a Bonferroni adjusted error ($\alpha=0.017$).

Within the context of the present invention, the expression "method for controlling ants" designs a method for eliminating or reducing ant populations present in a given area, or for reducing their activity.

When used in connection with the present invention, the expression "controlling agent" designs any component of the formulations of the invention which is capable of infringing direct or indirect damage to the ants, their colonies and/or the fungus which serves as their food supply, in such a way that the ant populations present in a given area are eliminated or reduced, or that their activity level becomes reduced.

The term "attractant" designs any ingredient which attracts the ants and which makes a formulation containing it to be identified as apt and desirable to be introduced in the ant nest.

The term "bait", as used herein, refers to a preparation comprising at least one controlling agent and one or more attractant, in such a way that ants carry it inside their nests.

When applied to the bait formulations used by the present invention, the term "supply" means to make said formulations available to the ants and outside the ant nest, in a way such that the ants can access the bait and carry its particles inside the ant nests.

When used within the context of the present invention, the expression "biological control agent" refers to viruses, microorganisms such as bacteria or fungi, or protozoans or nematodes which are pathogens of at least one of the stages in the life cycle of the ants, or that are pathogens of the *Leucoagaricus* fungus the ants feed on.

Used in connection with the biological control agent, the expression "propagation material" designs dispersal and resistance structures. Depending upon the biological control agent in question, the expression "propagation material" can make reference for example to one or more among viruses, spores, conidia, eggs or cysts.

In the methods disclosed herein, the difficulties arising from the delay rejection phenomenon in ants are overcame by means of sequentially administering or supplying different bait formulations containing at least one controlling agent. In order to avoid that the ants learn to associate the formulations of the present invention as a harmful item for the health or welfare of the colony, the formulations differ among them in at least one characteristic selected from consistence, texture, attractant and grain size, so the formulations are perceived as different resources by the ants.

For instance, at least one of the bait formulations used can be in the form of a gelatinous granulate and at least other of the formulations can be in the form of a dry pellet. By dry pellet it must be understood a granulated formulation of solid consistence (by opposition to a jelly consistence), in which the individual grains or pellets present low adherence to each other, and not necessarily a pellet in which the humidity content is extremely low or nonexistent. However, when the controlling agent contains conidia, dry pellets with a humidity content of 5% or less are preferred, as to prevent conidia germination before the formulation has been brought inside the nest.

In the case of dry pellets, using different ingredients and preparation techniques different textures can be obtained, which will contribute to provide a different aspect to the various formulations, increasing the diversity of possible formulations. For example, if in its preparation a powdered attractant is used, the texture of a pellet will be different than when using a liquid attractant.

Useful attractants in the context of the present invention are any natural or synthetic substance that attracts ants and induce them to identify the bait formulations as a resource suitable and desirable to be introduced into the nest, such as extracts or essential oils from various plants, or artificial fragrances.

Besides having a consistency, texture and attractant allowing that the ants identify the bait formulations as suitable resources to be brought into the nest, it is important that the grain size is appropriate for being carried by the ants. Formulations presented in the form of grains too large or too small will be carried at a slow pace —if small- or require group cooperation or in situ disaggregation—if too large— increasing the foraging cost for the colony and the time that the bait is exposed to demeaning environmental conditions. Grains that are too large or too small could not be taken, or can be partially carried into the ant nest, and therefore would not accomplish its function. In general, it is preferred that the bait formulations are granulates with a grain diameter between 2.5 and 5 mm.

The use of different colors of bait is also convenient as it facilitates identification by the user, assuring the correct execution of the method of the present invention.

According to the method of the present invention, bait formulations are supplied sequentially. That is, each formulation is provided spaced in time from the other formulations used in the method. Depending on the controlling agent used and on the degree of activity of the ants (which in turn depends from multiple factors such as weather and health of the colony), each formulation must be supplied between 5 and 10 days apart from the other. Preferably, each formulation is supplied 7 days after having supplied the previous one. Each formulation must be supplied a single time until completion of a cycle.

According to a particular embodiment of the method of the present invention, the formulation providing cycle is repeated once or more times, for instance, when persistence of ant activity is observed after performing one cycle of supplying. Preferably, each new supplying cycle is performed between 6 and 9 weeks after ending the previous cycle.

For example, in a preferred embodiment of the present invention one supplying cycle is performed in which 3 different bait formulations are used, administered with a 7-day spacing between each formulation. In an even more preferred embodiment, a second supplying cycle is performed 9 weeks apart from the last bait supplying of the previous cycle.

Each bait formulation used in the method of the invention may comprise a different controlling agent. However, because supplying different formulations prevents that the delayed rejection phenomenon and the colony's cleaning capacity result in an exposure to the controlling agent that is insufficient for the effective control of the ants, the method of the invention is particularly useful for achieving repeated or long-lasting exposure of the ants to a same controlling agent. Accordingly, in an embodiment of the invention, at least one controlling agent is present in all bait formulations used, and preferably two same controlling agents are present in all used formulations. In the case of formulations containing more than one controlling agent, or when formulations with different controlling agents are used, use of controlling agents acting negatively against each other must be avoided, preferring those which have a synergistic effect.

Controlling agents useful in the method of the present invention can be of different kinds. For example, the controlling agents can be synthetic pesticides or fungicides, plant substances or biological control agents. Among synthetic pesticides or fungicides, any of those which can be incorporated in a bait formulation without losing its activity can be used. There exist many pesticides well known in the art, as for example the insecticides aldrin, cypermethrine, chlorpyrifos, d-allethrine, deltamethrin, diflubenzuron, dodecachlorhydrate (Mirex), Mirex-S (a sulphamide), fenitrothion, fipronil, permetrine and other pyretroids and copper oxychlorine, and the fungicides dicloran, hexachlorobenzene, thiocarbamates, mancozeb, captan, copper oleate, copper phenylsalicilate, methylmercury, phenylmercuric acetate and cycloheximide, which are useful as controlling agents according to the method of the present invention.

Examples of plant substances useful as controlling agents within the context of the present invention can be grounds, extracts, essential oils, and secondary metabolites such as complex phenol compounds, saponines and alkaloids. The methods for obtaining extracts with high concentration of these substances are well known in the art, as for example alcohol extraction, acetone extraction, aqueous extraction, etc. For obtaining essential oils, direct pressing can be used when these are in large quantity in the starting material. Plant species from which substances of proven insecticide action can be obtained include *Gliricidia sepium* (madero negro), *Melia azedarach* (bead-tree), *Trichillia glauca* (trichillia), *Azadirachta indica* (neem), *Eucalyptus maculata* (eucalyptus), *Carapa guianensis, Cedrela fissilis* (Brazilian cedar), *Cipadessa fruticosa* and *Ricinus comunis* (castor oil plant). Plant extracts of proven antifungal activity have been obtained from the plants *Sesamum indicum* (sesame), *Virola* spp. (epená), *Otoba parvifolia, Citrus limonia* (lemmon tree), *Adiscanthus fusciflorus, Picramnia teapensis, Pilocarpus riedelianus, Pilocarpus grandiflorus* and *Trichillia* sp. (trichillia) (see Aubad López, P. 2010. *Plantas Usadas Por las Comunidades Indigenas Ticuna del PNN Amacayacu Para el Control de la Hormiga Cortadora: Evaluación Biológica y Búsqueda de Metabolitos Secundarios*. Tesis de Maestria en Ciencias-Quimica, Universidad Nacional de Colombia; and references therein).

When the formulations used in the present invention comprise biological control agents, said biological control agents are incorporated into the formulations in the form of propagation material. Propagation material particularly useful in the context of the present invention comprises dispersal and resistance structures such as for example viruses, spores, conidia, eggs or cysts, which can undergo the processes involved in the preparation of the formulations and withstand storage under a wide range of physic conditions and in many different chemical environments keeping a high degree of viability at the time in which they can develop. Biological control agents can be entomopathogens which act directly on the ants in at least one of their stages of development (egg, larva, pupa, adult), or mycopathogens acting on the ants indirectly, by negatively affecting the fungus of the genus *Leucoagaricus* that the ants grow and use as food supply. Non-limiting examples of entomopathogens useful in the present invention are several viruses which attack the ants, bacteria such as *Bacillus thuringiensis, Serratia marcescens* and *Wolbachia*; fungi such as *Purpureocillium* (ex *Paecilomyces*), *Beauveria, Metarhizium, Acremonium, Aspergillus, Entomophthora, Zoophthora, Pandora, Entomophaga*, and *Fusarium*; protozoans as for example *Kneallhazia* (ex *Thelohania*) and *Vairimorpha* and nematodes such as *Steinernema* and *Heterorhabditis*. Non-limiting examples of mycopathogens useful in the present invention are the fungi *Rizhopus, Cunnighamella, Escovopsis, Trichoderma, Syncephalastrum, Verticillium (Lecanicillium), Gliocladium* and *Purpureocillium (=Paecilomyces)*.

As mentioned above, the method of the invention is particularly useful for achieving a repeated or long-lasting exposure of the ants to a same controlling agent, for which reason in a preferred embodiment of the invention at least a same biological control agent is present in all bait formulations used. In an even more preferred embodiment, it is preferred that each bait formulation comprises a different strain of the biological control agent, profiting from said biological control agent natural variability, thus achieving a more complete effect on the ant colonies.

Different biological control agents can be combined within a same formulation. For example, in a preferred embodiment of the present invention, all used formulations comprise the same two biological control agents. In an even more preferred embodiment, all formulations comprise an entomopathogen and a mycopathogen, the entomopathogen and the mycopathogen being the same in all formulations.

The precaution of avoiding negative interactions between controlling agents also applies to the combination of two or more biological control agents, both in a same formulation or in different formulations within a kit. Thus, when one or more formulations used in the present invention combine an entomopathogen that is a fungus which attacks ants and a mycopathogen, the mycopathogen advantageously shows specificity for the *Leucoagaricus* fungus used by the ants as food supply, in order to minimize the potential negative interaction that could occur between a mycopathogen and an entomopathogenic fungus due to the negative action of the first over the second. Accordingly, in a preferred embodiment of the present invention, the formulations used comprise conidia of an entomopathogenic fungus, for example *Purpureocillium (=Paecilomyces), Beauveria, Metarhizium, Acremonium, Aspergillus, Entomophthora, Zoophthora, Pandora and Entomophaga*, and conidia of a mycopathogenic fungus showing specificity for the *Leucoagaricus* fungus used by the ants as food supply. More particularly, an embodiment in which the formulations comprise conidia of *Purpureocillium lilacinum* and of *Escovopsis* sp. is preferred. Use of *Escovopsis* is also preferred because the inventors have discovered that the growth rate and conidiation levels of this fungus increase in the presence of *Leucoagaricus*. This increase in growth and conidiation rate not only make *Escovopsis* more efficient for destroying cultures of *Leucoagaricus* but also allows to increase *Escovopsis* conidia production by adding small pieces of *Leucoagaricus* to the growth medium of *Escovopsis*. Formulations in which *Purpureocillium lilacinum* and *Escovopsis* sp. are combined are further particularly preferred because the inventors have discovered a previously unreported necrotic effect of *Purpureocillium lilacinum* over *Leucoagaricus*, adding a new and unexpected necrosing activity precisely on the *Leucoagaricus* fungus on which the ants feed to its entomopathogenic activity. As a matter of fact, this double action makes of *Purpureocillium lilacinum* a preferred controlling agent in formulations like the ones in the present invention even if they have a single biological control agent.

The propagation material of the biological control agent/agents must be present in the formulations minimally at concentration so as to produce a noticeable effect in terms of elimination or reduction of the ant populations present in one area, or in terms of reduction of their activity level. Below said minimal concentration, the negative effect in the ant populations size or the activity level of their colonies will be insignificant. On the other hand, there is a maximum in the concentration of biological control agent propagation material above which an increase in the concentration does not result in a significant increase in the reduction of ants populations or their colonies activity level. Minimal and maximum propagation material concentration would depend on the particular kind of controlling agent and on the number of controlling agents present in the formulation, but in general bait formulations in which the controlling agent/s propagation material is between $10^3$ and $10^{10}$ propagation structures per gram of formulation are preferred. In particular, when the biological control agents are fungi, formulations with conidia concentrations between $10^6$ and $10^9$, and more particularly between $10^8$ and $10^9$ viable conidia per gram of formulation are preferred.

Kits combining different formulations used in the method of the present invention on its various embodiments are also part of the present invention. The invention kits comprise at least two bait formulations containing at least one controlling agent for the ants. Such formulations differ among them at least in one characteristic selected from consistence, texture, attractant and grain size. Additionally, in order to allow a better differentiation among them, the used formulations that are part of the kits of this invention can be of different colors, which can be achieved for instance by using colorants known in food and baking industries. In one of its preferred embodiments, the kits consist of three different bait formulations.

Each bait formulation within a kit can have a different controlling agent. However, in order to obtain a massive effect and overcome the cleaning capacity of the colony, kits in which at least one controlling agent is the same in all formulations are preferred. The controlling agents can be synthetic pesticides or fungicides, plant extracts which are noxious for the ants or for the fungus they use as food supply, or biological control agents, preferring the two last over the first because their environmentally friendly properties.

The biological control agents are present in the bait formulations which are part of the kits of the present invention in the form of spores, conidia, cysts, eggs or other resistance and/or dispersal structures which may act as propagation material. The propagation material is preferably at a concentration between $10^3$ and $10^{10}$ viable conidia/gr of formulation, more preferably between $10^6$ and $10^9$, and even more preferably between $10^8$ and $10^9$ viable conidia/gr of formulation. Preferably, the formulations which are part of the kits of the invention can comprise an excipient which favors germination of the propagation material, as for example corn starch, sugar, confectioner's sugar, oats, chitin, or any other which may fulfill the same function. Using germination media provides an additional textural variation element, as different germination media will give the bait formulations different consistence, hardness and texture.

When a same biological control agent (which can be an entomopathogen or a mycopathogen) is present in all bait formulations in a kit, each formulation preferably contains a different strain, variety or ecotype of the biological control agent.

One or more of the formulations which are part of the kits of the present invention can comprise a combination of more than one controlling agent. For instance, one or more formulations within a kit according with the present invention can contain a plant extract and propagation material of a biological control agent as controlling agents. Nevertheless, when a given same formulation contains two or more controlling agents, or even when different controlling agents are present in different formulations within a same kit, it is important avoiding combinations in which one of the controlling agents affects negatively the other. For example, if a pesticide and a biological control agent are combined, those should be selected in such a way that the pesticide does not act negatively on the biological control agent propagation material or on the organisms developing from it within the ant nest.

In one of its particular embodiments, the kits of the present invention comprise bait formulations of gelatinous consistence. Several kinds of alginate with different cations and viscosity degrees, agar or any other gelling agent known in the art can be used for preparing this kind of formulation. A formulation of this kind can be obtained for example by adding to the alginate a solution containing the controlling agent and the attractant, preferably a liquid attractant, before precipitating the alginate or pelleting.

It is also possible that at least one of the formulations of the kit of the invention is in the form of a dry pellet. By dry pellet it must be understood a granulate with a solid consistence (as opposed to a gelatinous consistence), in which the individual grains or pellets present low adherence among them, and not necessarily a pellet in which the humidity content is extremely low or zero. Dry pellets can be obtained from a dough formed by using one or more inert fillers such as bentonite, talc, xanthan gum, guar gum, or any functional equivalent, and one or more liquid media such as soybean oil, distilled water, saline solution, or any other suitable liquid medium.

Both the gelatinous formulation and those in the form of a dry pellet are provided in granulated form, preferably with a grain diameter between 2.5 and 5 mm.

The bait formulations which are part of the kits of the present invention contain one or more substances that attract ants, or attractants, which mask the controlling agent and facilitate the identification of the bait by the ant as an apt and desirable resource to be brought into the nest. The attractant can be mixed with the rest of the bait formulation ingredients, although bait formulations where the attractant is also or exclusively present as a covering or coating of the formulation grains are preferred. In an even more preferred embodiment, the formulation grains are coated with a sugary covering or coating containing one attractant. According to this embodiment, the attractant can be present only in the sugary coating, or the formulation may also contain the same or other attractant incorporated within the matrix that forms the grain nucleus (as opposed to the coating). The sugary nature of the coating works as a powerful additional attractant. The attractant on each formulation that is part of a kit is different from the attractant present in the other formulations of the same kit. Substances acting as attractants can be obtained from plants usually consumed by leaf-cutting ants, preferably plants preferred by the ants. As an example, the attractant can be selected from the group consisting of alcoholic extracts or powder of skin, pulp, or albedo of citrus fruits such as orange, grapefruit or tangerine; leaves preferred by the ants; and rose petals. Alcoholic extracts can be obtained by macerating fresh material in a solvent such as ethanol. Attractants in the form of dry powder can be obtained for instance by drying plant material in a stove at 40-50° C. followed by grinding until obtaining a fine powder.

By studying the properties of the several control agents useful in the context of the present invention, the inventors have surprisingly found that *Escovopsis* growth rate and conidiation increase when this fungus is grown in the presence of pieces of the fungus *Leucoagaricus*.

Even more surprisingly, said increase (although in a lesser degree) is observed when pieces of medium (i.e. PDA) free of micelia but coming from a *Leucoagaricus* culture are added to the culture medium of *Escovopsis*. The increase in conidiation in absence of *Leucoagaricus* micelia suggests that the induction is produced by means of some kind of compound produced by *Leucoagaricus*, which is also present in the medium free of micelia and that can be detected by *Escovopsis*. Accordingly, it is an object of the present invention a method for inducing conidiation in *Escovopsis*, wherein conidiated and non-conidiated micelia of the fungus *Leucoagaricus*, or fragments of medium with conidiated and non-conidiated micelia of the fungus *Leucoagaricus*, or fragments of medium (free of micelia) coming from *Leucoagaricus* cultures are added to the *Escovopisis* culture medium.

This conidiation induction method is particularly advantageous when use of *Escovopsis* as control agent is pursued.

The several aspects of the present invention will be better understood through the following examples. The scope of the invention, however, is not limited to the examples, as the purpose of these is not to limit the invention but to illustrate particular embodiments of the invention from which alternative embodiments will be evident for those skilled in the art.

Example 1

Obtaining of Entomopathogenic and Mycopathogenic Fungi

From leaf-cutting ant colonies in the field, the fungi *Escovopsis weberii* (from *Acromyrmex lundii* colonies), *Purpureocillium lilacinum* (from *Acromyrmex lobicornis* colonies), *Trichoderma harzianum* (from *Acromyrmex striatus* colonies) and *Beauveria bassiana* (from *Acromyrmex lundii* colonies) were isolated. For isolating *Trichoderma harzianum* and *Escovopsis* a minimal part of the material present in the surface of the garden where the ants cultivate the *Leucoagaricus* sp. was taken with the tip of a dissection needle and used to inoculate PDA (potato dextrose agar) medium supplemented with penicillin G and streptomycin (100 U/ml and 50 mg/ml, respectively). For obtaining the entomopathogens *Purpureocillium lilacinum* and *Beauveria bassiana*, specimens of *Acromyrmex lundii* that were walking in the colony paths were collected. At the lab, the ants were individually put in a wet chamber, which consists in a small chamber containing a paper moistened with sterile distilled water. Upon death, specimens presenting mycelia growing from the integument were identified with the help of a stereoscopic microscope. Then, mycelia were taken from the body of the ant with the tip of a dissection needle, seeding with these a petri dish with PDA (potato dextrose agar) supplemented with penicillin G and streptomycin (100 U/ml and 50 mg/ml, respectively) and growing it for 7 days. The obtained microorganisms were first identified by its morphology on the culture dish. These identifications were then corroborated by optical microscopy. For enhancing visualization vital staining with Methylene Blue and Floxin was used, and for cell-wall staining Congo red was used. Once purified and identified, the fungi were stored at −80° C. until used.

Example 2

Obtaining of Conidia Starting Stock

Production of conidia was carried out according to the methods described in *Manual of techniques in insect pathology* (Lacey L. A. 1997. Academic Press, London Lacey, 1997). Briefly, for *Purpureocillium lilacinum, Trichoderma harzianum, Escovopsis weberii* and *Beauveria bassiana* conidia production, Petri dishes with PDA were inoculated with small portions taken with an inoculation loop from frozen-stored samples obtained in the Example 1, and pure cultures were grown for 7 days. After this period of time, micelia with conidia were extracted and put into a Falcon tube with 30 ml of Tween 80 0.01 v/v. It was agitated by vortex until a homogeneous solution was obtained. From 1 ml of this solution serial dilutions were performed until obtaining a conidia concentration of between 6 and $6.5 \times 10^7$ conidia/ml, as measured with Neubauer chamber. The solution was immediately used.

Example 3

Activity of *P. lilacinum* on *A. lundii* Ants

*Acromyrmex lundii* ants were subjected to three different treatments. One group of 60 ants, per each of the 6 colonies, was immersed for 10 seconds in a suspension of *P. lilacinum* conidia (isolations P01, P02 and P05) in water at a concentration of $1 \times 10^5$ conidia/ml. A second group was immersed in water alone, and a third group was not subjected to immersion. Survival of ants on each group was recorded. As it can be seen in FIG. 1, ants exposed to the suspension of *P. lilacinum* conidia showed a survival rate significantly lower than that shown by controls with water alone and with no water. In 10-12 days almost all ants treated with the conidia suspension were dead, with *P. lilacinum* explaining 70% of the deaths.

Example 4

Evaluation of the Effect of *Leucoagaricus* Over *Escovopsis* Growth

Small pieces of *Leucoagaricus* from three different isolations (N from 6 to 16 per isolation) were grown in Petri dishes until attaining an area of 6.5 cm$^2$. These plates were used for performing challenges by placing a piece of agar with *E. weberii* covered by mature conidia. Controls (N=6) were made both for each isolation of *Leucoagaricus* and of *E. weberii*, growing alone. The area covered by each fungus was measured every 12 hours for 6 days, recording the presence of conidia and conidiation degree. The conidiation degree was measured as the area of the Petri dish covered by conidia. The assay was terminated when *Escovopsis weberii* completely covered the Petri dish.

For demonstrating that *E. weberii* induction resulted from detection of an agar-diffusible compound produced by *Leucoagaricus* the following experiment was performed. 12 Petri dishes were prepared with PDA to be used as experimental group. In the center of these plates it was added a 1 cm$^2$ piece of agar extracted from the micelia-free part of a Petri dish in which *Leucoagaricus weberii* had been grown for 45 days and occupied at least 75% of the area. Then the plates were inoculated in the edge of the plate with a 1 cm$^2$ piece of agar with non-conidiated micelia of *Escovopsis weberii*. As positive control, 12 Petri dishes were prepared in a similar manner but in which the agar coming from the *Leucoagaricus* cultures contained micelia instead of being free of them, and as negative control 12 Petri dishes were used in which no agar coming from *Leucoagaricus* sp. cultures was added. The assay was repeated but inoculating *Escovopsis weberii* with mature conidia, as to assess if the effect of an eventual conidiation induction was transitory or long-lasting. The proportion of conidiated Petri dishes for each treatment and assay was compared with the T proportion test.

Figure 2:
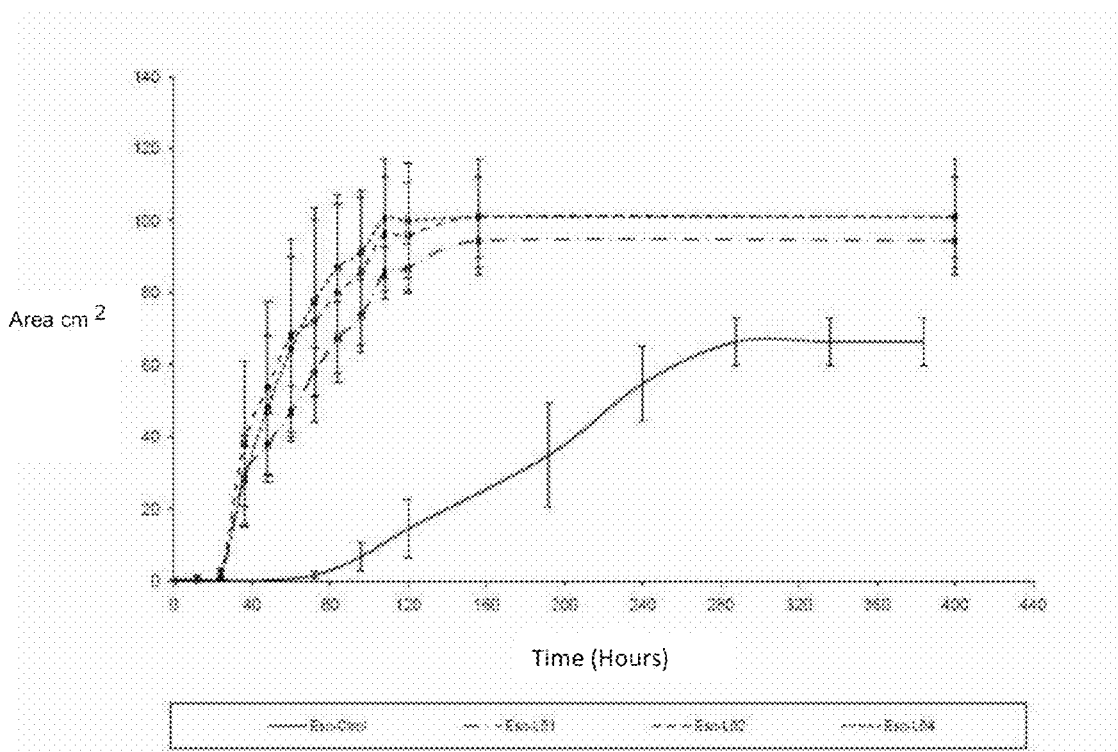
FIG. 2 shows the growth rate of *Escovopsis weberii* alone (Esc-Ctrol) and in the presence of three different strains of *Leucoagaricus* sp. (Esc-L01, Esc-L02, Esc-L04) as described in Example 4.
Figure 3:
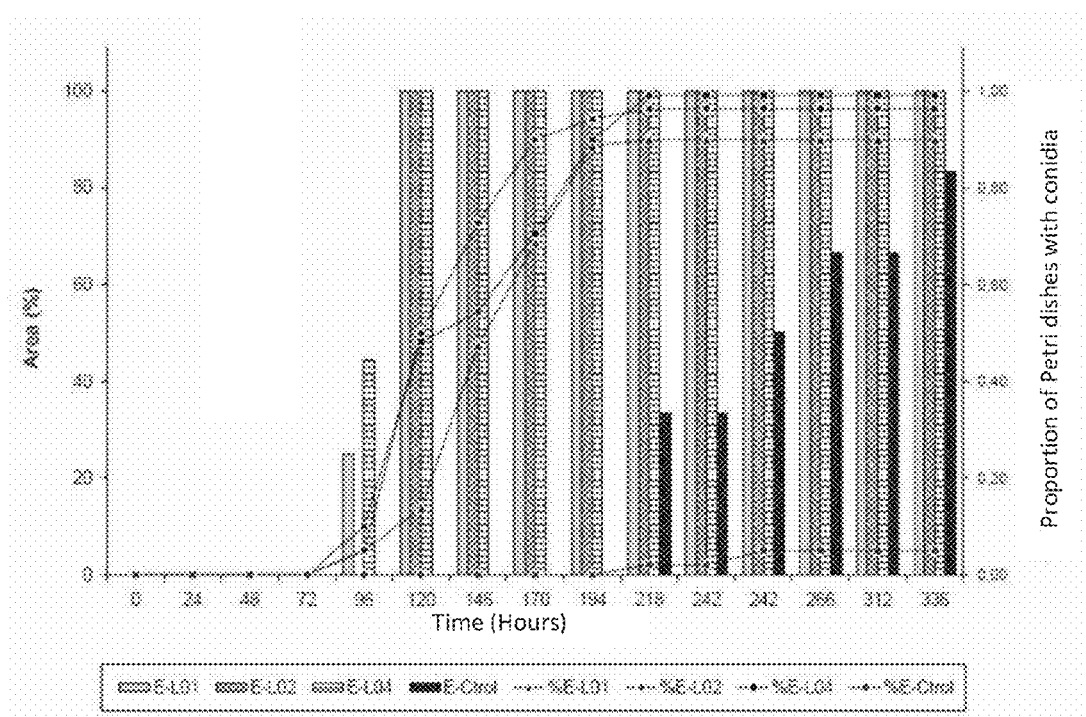
FIG. 3 shows the conidiation degree of *Escovopsis weberii* (curves) when grown alone (E-Ctrol) and in the presence of three different strains of *Leucoagaricus* sp. (Esc-L01, Esc-L02, Esc-L04) as described in Example 4.
Figure 4A:
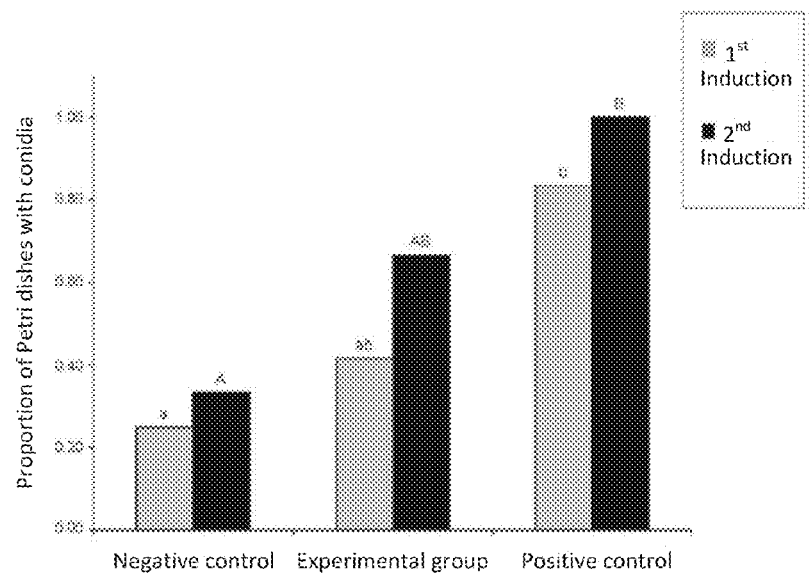
FIG. 4a shows the conidiation degree of *Escovopsis weberii* when grown alone (negative control) and in the presence of PDA fragments with (positive control) and without (experimental group) *Leucoagaricus* sp. micelia coming from *Leucoagaricus* sp. cultures as described in Example 4.
Figure 4B:
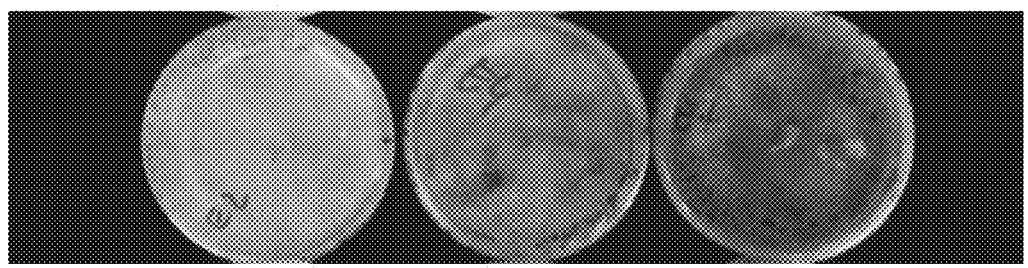
FIG. 4b shows the conidiation degree of *Escovopsis weberii* when grown alone (left) and in the presence of PDA fragments with (right) and without (center) *Leucoagaricus* sp. micelia coming from *Leucoagaricus* sp. cultures as described in Example 4.

Results are shown in FIGS. 2 to 4. As it can be seen in FIG. 2, all *Escovopsis weberii* cultures in the challenges attained stationary phase significantly faster and with a larger final area than their control, with the three isolations of *Leucoagaricus*. Moreover, the experimental group showed a significantly larger area covered with mature conidia than the negative control (curves in FIG. 3). In conclusion, *E. weberii* grows faster and produces more conidia in the presence of *Leucoagaricus* than when growing alone.

No significant differences were found in the percentage of conidiated Petri dishes or in the conidiation degree/plate between each control group and the experimental group ($p>0.09$) but a significant difference was found between both control groups ($p<0.016$). Repetition of this assay but with conidiated *E. weberii* showed the same results pattern, but presenting an even larger conidiation degree respect to the previous assay (FIG. 4). This demonstrates that there is a substance produced by *Leucoagaricus* that is detected by *E. weberii*, inducing its higher conidiation.

Example 5

Interaction Between *Purpureocillium lilacinum* and *Escovopsis weberii*

Figure 5:
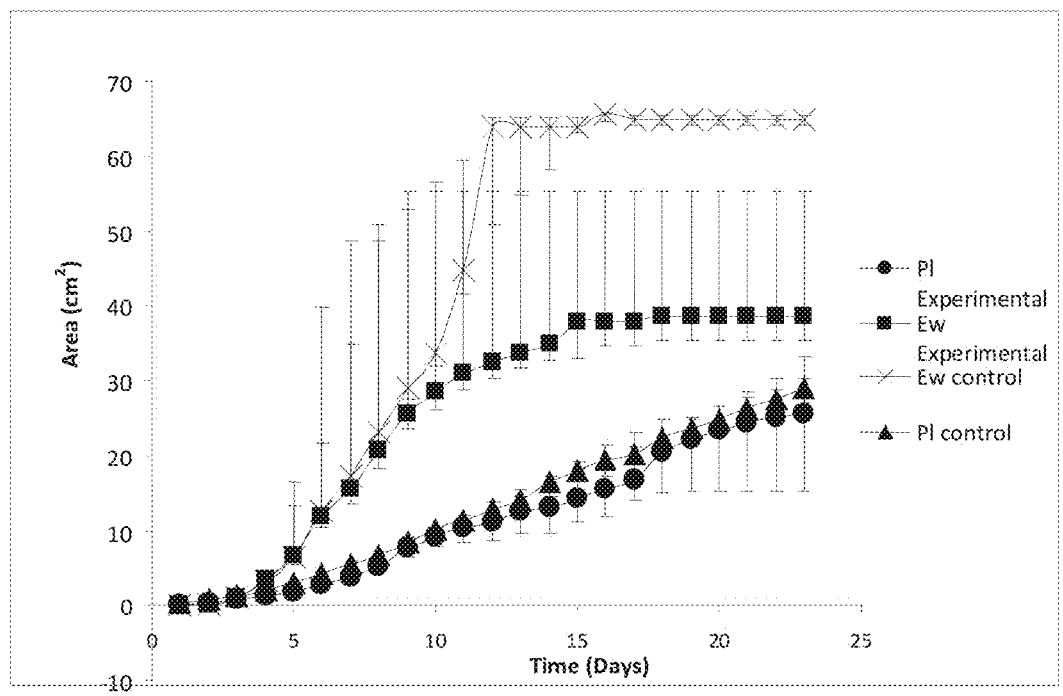
FIG. 5 shows growth kinetics for *P. lilacinum* (Pl) and *E. weberii* (Ew) growing together (experimental) and separately (control) as described in Example 5.

*E. weberii* and *P. lilacinum* conidia suspensions were prepared, both with a concentration of $1\times10^5$ conidia/ml. Opposite ends of culture plates were inoculated with 10 µl of each suspension (challenges). Two control groups were also created by inoculating plates with only one or the other fungus. Once the essay started, the growth area of the fungi was measured daily in order to evaluate its growing kinetics. Results are shown in FIG. 5.

These results show that for *P. lilacinum*, growth when cultured alone and in the experimental group are similar. Growth of *E. weberii*, on the other hand, is significantly greater when it grows alone than when in the presence of *P. lilacinum*, but in both cases its growth rate is higher than that of *P. lilacinum* growing alone or co-cultivated.

Figure 6A:
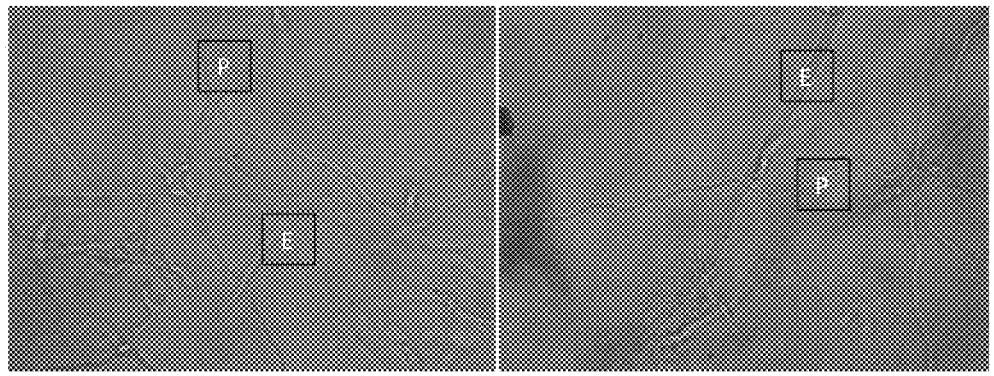
FIG. 6a shows two pictures of *Purpureocillium lilacinum* and *Escovopsis weberii* growing together as described in Example 5. In both pictures (40×) *P. lilacinum* and *E. weberii* hyphae 72 hs after inoculation are observed.

For analyzing if there was a necrotrophic effect between both fungi, slides were covered with a fine layer of PDA, which were then inoculated with both fungi, one on each end, covering with a cover glass. Then interaction among hyphae was observed daily under optical microscope. As it can be seen in FIG. 6a, there is no necrotic effect between the fungi, suggesting that the negative effect of *P. lilacinum* on the growth rate of *E. weberii* is due to competition for the substrate.

Figure 6B:
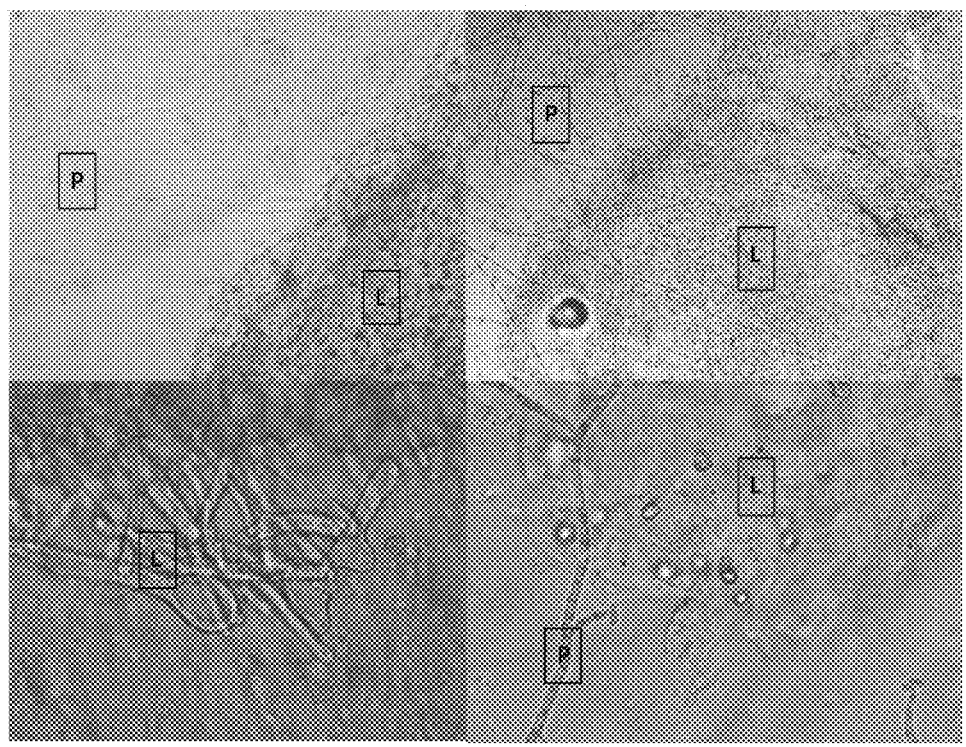
FIG. 6b shows pictures of combined cultures of *Purpureocillium lilacinum* (P) and *Leucoagaricus* sp. (L) as described in Example 5. The pictures on the left show areas of the microculture two days after started. The pictures on the left show the same areas 4 days after starting the culture, where it can be seen that *Leucoagaricus* sp. hyphae show necrosis. Pictures at the top are at a 10× magnification while pictures on the bottom are at 40× magnification.

For analyzing if there was a necrotrophic effect between *Purpureocillium lilacinum* and *Leucoagaricus*, slides were covered with a fine layer of PDA, which were then inoculated with both fungi, one on each end, covering with a cover glass. Then interaction among hyphae was observed daily under optical microscope. As it can be seen in FIG. 6b, there is a necrotic effect of *Purpureocillium lilacinum* on *Leucoagaricus*.

Example 6

Mass-Production of Conidia

Mass-production of *Purpureocillium lilacinum*, *Trichoderma harzianum*, *Beauveria bassiana*, and *Escovopsis weberii* fungi conidia was carried out in 500 cm$^3$ glass flasks containing 50 g of rice and 25 ml of distilled water. The flasks were covered with tin foil and sterilized for 20 minutes. Afterwards, each flask was inoculated with 150 µl of the conidia suspension obtained in Example 2. The flasks were incubated in a growth room at a temperature of 25° C. and 60% RH for 10 days.

Example 7

Attractant Obtention

For producing citrus fruit attractants 170 gr of skin in 750 ml of ethanol 70% v/v. Citric fruits employed were orange, grapefruit and tangerine. For producing rose extract, 100 rose petals were placed in 750 ml of ethanol 70% v/v.

In all cases, they were left macerating for 15 days in bottles covered with tin foil, as to avoid contact with light. After 15 days, it was filtered and the liquid fraction was stored in refrigerator in an amber bottle until use.

Citropulp was prepared from orange peel, which was ground and then dried using a 500 w lamp overnight.

Example 8

Formulations Preparation

Different bait formulations were prepared using the following ingredients and proportions:

FP (orange extract): 250 g of PDB (potato dextrose broth), 7 g of xantic gum, 200 g of rice, 350 g of cornmeal, 70 g of corn starch.

FAV (rose extract): 250 g of PDB (potato dextrose broth), 7 g of xantic gum, 100 g of rice, 300 g of oats, 40 g of wheat flour, 40 g of corn starch.

FPN (grapefruit extract): 250 g of PDB (potato dextrose broth), 7 g of xantic gum, 100 g of rice, 400 g bread crumbs, 25 g of corn starch.

FG (tangerine extract): 250 g of PDB (potato dextrose broth), 7 g of xantic gum, 100 g of rice, 650 g of wheat flour.

FC: 273 g of citropulp (dry orange peel); 223.2 g of confectioner's sugar; 12 g of flavorless gelatin; 21.6 g of industrial talc; 91.2 g of soybean oil; y 216 g of corn starch.

FM: 350 g of confectioner's sugar; 350 g of corn starch; 20 g of industrial talc; 200 g of soybean oil; 26.6 ml of extract (of tangerine, grapefruit, orange or rose); y 73.4 ml of water.

FAR: 0.1 g of sodium alginate 1.2, 10 ml of saline solution 0.9%, 250 µL of extract (rose, grapefruit, tangerine or orange), calcium chloride solution 0.1 M.

FAR chitin: 0.4 g of sodium alginate 1.2, 1 gr of chitin, 20 ml of saline solution 0.9%, 520 µL of rose extract, calcium chloride solution 0.1 M.

FAR oats: 0.4 g of sodium alginate 1.2, 1 gr of oats, 20 ml of saline solution 0.9%, 520 µL of rose extract, calcium chloride solution 0.1 M.

FAR sugar: 0.4 g of sodium alginate 1.2, 1 gr of confectioner's sugar, 20 ml of saline solution 0.9%, 520 µL of rose extract, calcium chloride solution 0.1 M.

FAR corn starch: 0.4 g of sodium alginate 1.2, 1 gr of corn starch, 20 ml of saline solution 0.9%, 520 µL of rose extract, calcium chloride solution 0.1 M.

For the first four formulations, inert ingredients and fillers were mixed with the rice coming from the fermentation flask of Example 6, according to the compositions in Table 1. Once a uniform mixture was obtained, it was manually modeled into grains of about 2.5 and 5 mm. These formulations (FP, FAV, FPN y FG) were additionally coated with a coating containing an attractant. For such purpose, the formulations were allowed to dry for two hours and then were coated by pouring over them a coating mixture obtained by mixing 250 g of confectioner's sugar, 100 g of corn starch, 17 g of attractant extract (which varies for each formulation as indicated above), and water as needed. Afterwards, coated granulates were dried for two days at room temperature; then, they were re-granulated as to obtain a uniform particle size.

In the case of the 5 FAR formulations, a conidia suspension was prepared, and then added to a mixture with the sodium alginate, the saline solution, the extract (rose, grapefruit, tangerine or orange) and the chitin, oats, sugar or corn starch depending on the case. This mixture was added dropwise over the calcium chloride solution.

FM and FC were allowed to dry for 24 h. before using.

TABLE 1

Composition of the granulated bait formulations used in Examples 9 to 14.

| Formulation | Filler | | Active ingredient | Inhert ingredient/excipient | | Attractant | Gelling agent |
|---|---|---|---|---|---|---|---|
| FP | Water or PDB | Xantan gum | | Cornmeal | Corn starch | Orange extract | |
| FPN | Water or PDB | Xantan gum | Rice + active ingredients | Bread crumbs | Corn starch | Grapefruit extract | |
| FAV | Water or PDB | Xantan gum | Rice + active ingredients | oats | Corn Flour starch | Rose extract | |
| FG | Water or PDB | Xantan gum | Rice + active ingredients | Flour | | Tangerin extract | |
| FC | Water | Soybean oil | | Confectioner's sugar | Corn Industrial starch talc | Citropulp | Flavorless gelatin |
| FM | Soybean oil | | | Confectioner's sugar | Corn Industrial starch talc | Orange, grapefruit, tangerine or rose extract | |
| FAR | Sodium alginate | | | | | Orange, grapefruit, tangerine or rose extract | Calcium chloride 0.1M |
| FAR chitin | Sodium alginate | | | Chitin | | Rose extract | Calcium chloride 0.1M |
| FAR corn starch | Sodium alginate | | | Corn starch | | Rose extract | Calcium chloride 0.1M |
| FAR sugar | Sodium alginate | | | Confectioner's sugar | | Rose extract | Calcium chloride 0.1M |
| FAR oats | Sodium alginate | | | Oats | | Rose extract | Calcium chloride 0.1M |

Example 9

Viability Assays

For determining the concentration of the controlling agent in the bait formulations FG, FPN, and FAV of Example 8, expressed as viable conidia/gram of formulation, one gram of each granulate was measured, by sextuplicate (n=6), and each gram was homogenized in 10 ml of sterile distilled water in a Falcon tube. The grains were left one hour in the liquid and then were agitated in vortex for a minute as to assure its dissintegration, a better conidia yield and homogeneous mixing thereof. Afterwards, serial dilutions were performed and for each replication (N=6) 100 µl of dilution 1/1000, 100 µl of dilution 1/100000 and 100 µl of dilution 1/1000000 (dilutions −3, −5 and −6) were inoculated in Petri dishes with PDA medium using Grigasky spatula. Number of Colony Forming Units was measured daily. One CFU was taken as a viable conidium. In Table 2 maximum values measured for each formulation are shown.

TABLE 2

Conidia concentration in bait formulations (viable conidia/gr of formulation). Conidia of *Purpureocillium lilacinum* (Pl) *Beauveria bassiana* (Bb), *Trichoderma harzianum* (Th) were used.

| FG | | | FPN | | | FAV | | |
|---|---|---|---|---|---|---|---|---|
| Pl | Bb | Th | Pl | Bb | Th | Pl | Bb | Th |
| 2.8E+7 | 1.00E+7 | 2.00E+06 | 8.6E+08 | 2.5E+7 | 2.6E+08 | 1.8E+08 | 3.00E+07 | 2.00E+07 |

Example 10

Trials of Consumption of FM and FC Formulations by Lab Colonies

A simultaneous choice test was performed for bait formulations orange FM lime color, tangerine FM yellow color, rose FM pink color, pomegranate FM green color, and orange FC prepared as in Example 8. 5 g of each formulation were placed on container of the lab colony assigned to the plant matter. Activity and number of formulation transported were measured every 5 minutes for more than 2 hours (70 minutes), the time elapsed until the first grain was transported and the time elapsed until the first grain was placed on the fungus.

Figure 7:
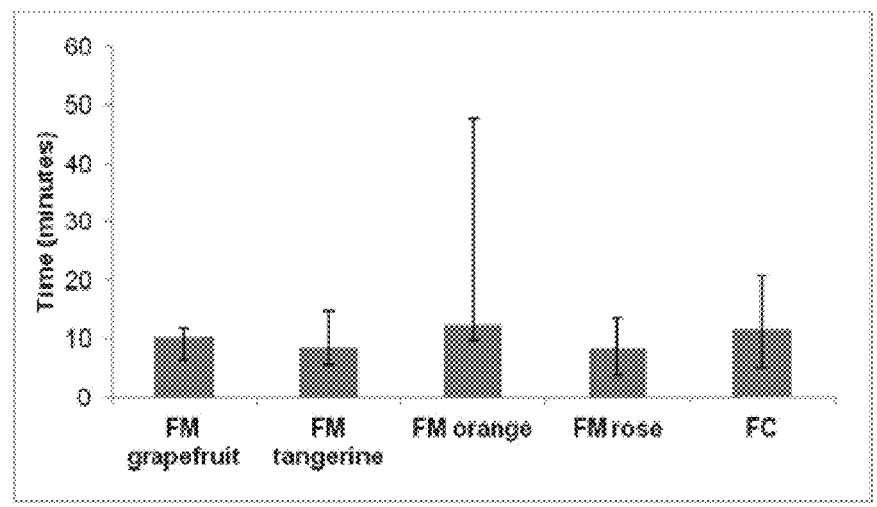
FIG. 7 shows time elapsed until the first grain of formulation was transported by the ants (as median and as 25 and 75% quartiles) in the assays of Example 10.
Figure 8:
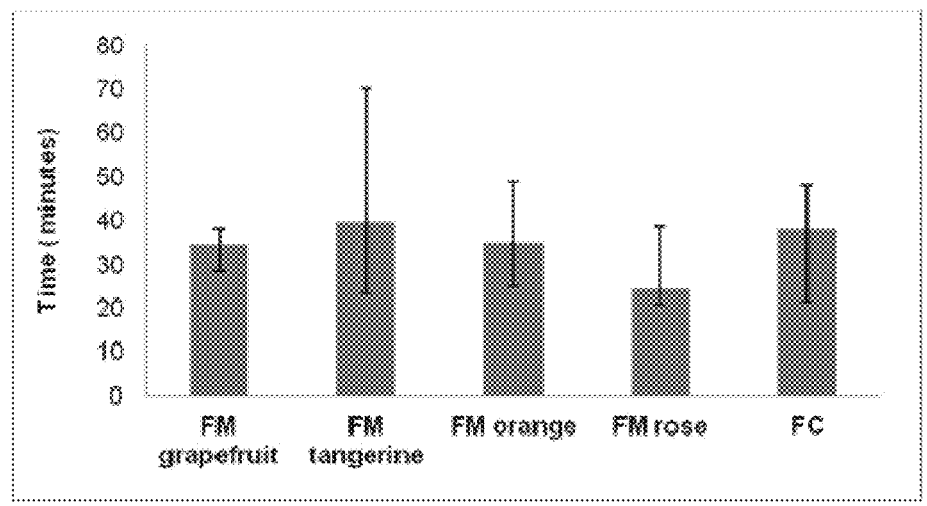
FIG. 8 shows time elapsed since the first grain of formulation was transported by the ants until the first grain of formulation was placed in the fungus (as median and as 25 and 75% quartiles) in the assays of Example 10.
Figure 9:
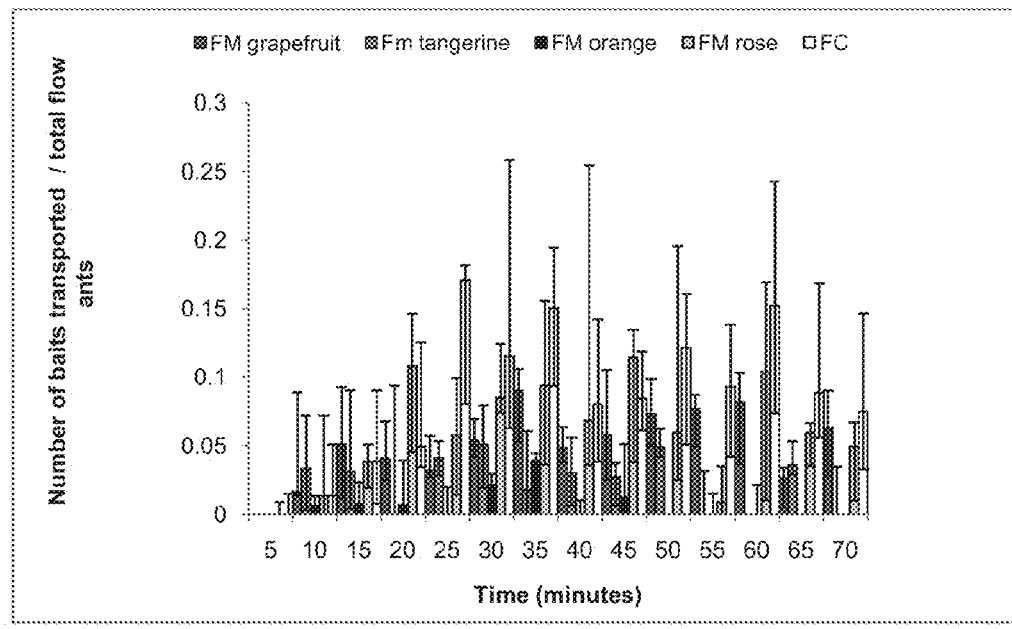
FIG. 9 shows the number of transported grains (as median and as 25 and 75% quartiles) relative to ant total flow, as a function of the time in the assays of Example 10.
Figure 10:
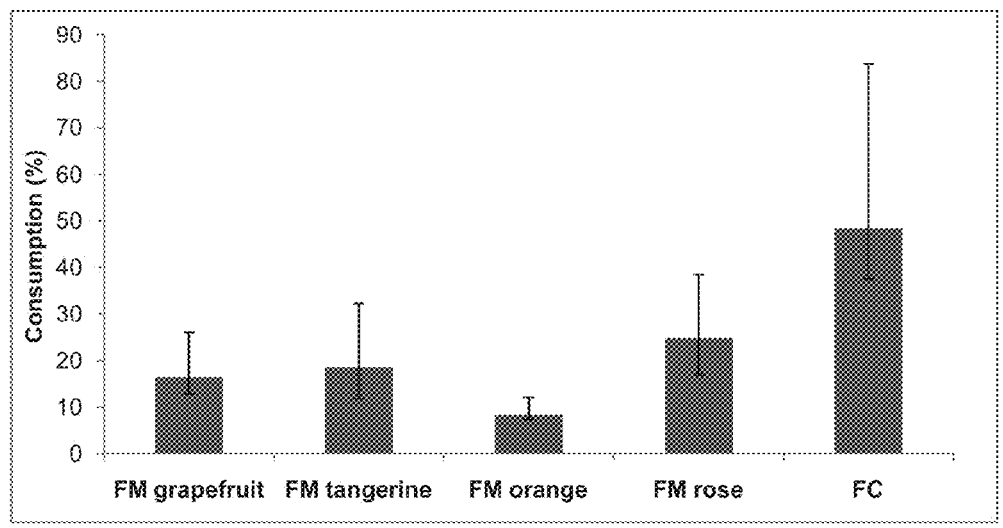
FIG. 10 shows consumption (in percentage, as median and as 25 and 75% quartiles) of the different types of formulations provided in the assays of Example 10.

All types of formulations were transported for the first time at about 10 minutes, with Orange FM being the one showing the larger dispersion for this parameter (FIG. 7). Regarding the time elapsed since the first grain of formulation was transported until the first grain was placed on the fungus that serves as food, depending on the formulation a delay of between 25 and 40 minutes was recorded, with rose FM being the one showing the shortest time and the lower dispersion for the recorded measurements (FIG. 8). Regarding the number of grains transported corrected by the ants activity, FC and rose FM were the ones with the highest values, and orange FM the one with the lowest value (FIG. 9). The same pattern was obtained for formulation consumption (measured as the percentage of the weight obtained at the end of the trial relative to the total amount placed) (FIG. 10). Thus, the larger carrying was directly related to a larger consumption. As conclusion, FC and rose FM formulations were chosen as the best candidates based on these results.

Example 11

Trials of Consumption of Alginate (FAR) Formulations by Lab Colonies

FAR formulations of the Example 8, containing different kinds of extracts (rose, grapefruit, tangerine and orange) were tested in 6 lab colonies (3 with queen, 3 without queen). A simultaneous choice test was performed as explained in Example 10, taking the same measurements, but this time 60 beads of each formulation were placed in the container assigned to the plant material.

Formulations based on sodium alginate with different extracts had different colors: pink for rose, green for grapefruit, yellow for orange, and orange for tangerine.

After selecting the most attractive extract, versions of the same formulation were prepared but adding different inert substances. It was thus prepared with 0.4 g sodium alginate 1.2, 20 ml of saline solution 0.9%, 520 µl of rose extract with 5 ml of oats 20% w/v in water (or 1 g of chitin, or 1 g of confectioner's sugar, or 1 g of corn starch).

50 beads of each formulation were placed in the container assigned for the plant material. 6 lab colonies were used (3 with queen, 3 without queen). As before, measurements of activity and number of formulation grains or beads were taken every 5 minutes for more than 2 hours (70 minutes), elapsed time until the first grain was transported and elapsed time until the first grain was placed on the fungus.

Figure 11:
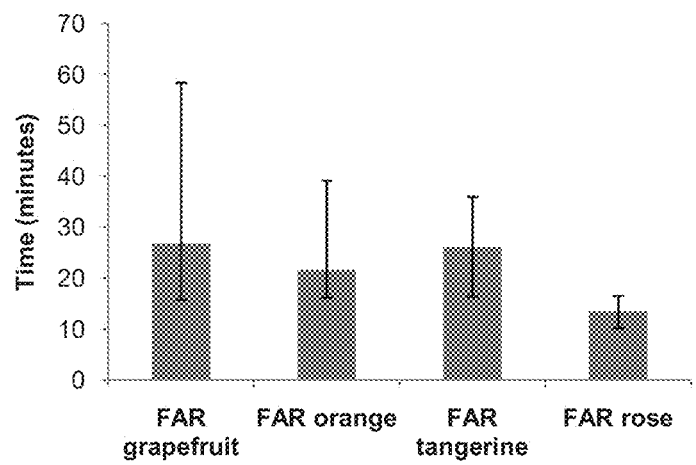
FIG. 11 shows time elapsed since administration of the bait until the first grain of formulation was transported by the ants (as median and as 25 and 75% quartiles) in the assays of Example 11.
Figure 12:
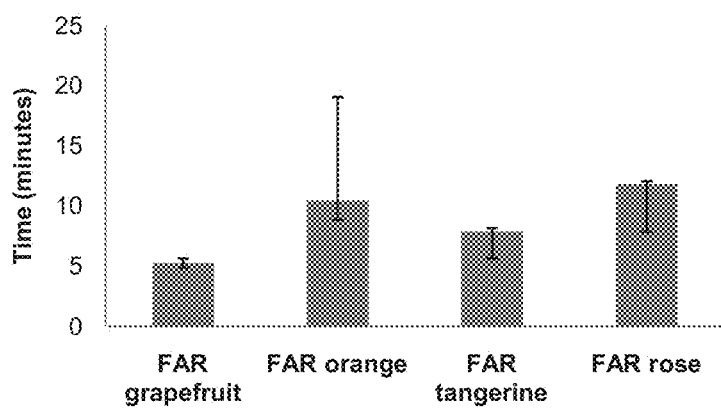
FIG. 12 shows time elapsed since the first grain of formulation was collected until the first grain of formulation was placed in the fungus (as median and as 25 and 75% quartiles) in the assays of Example 11.
Figure 13:
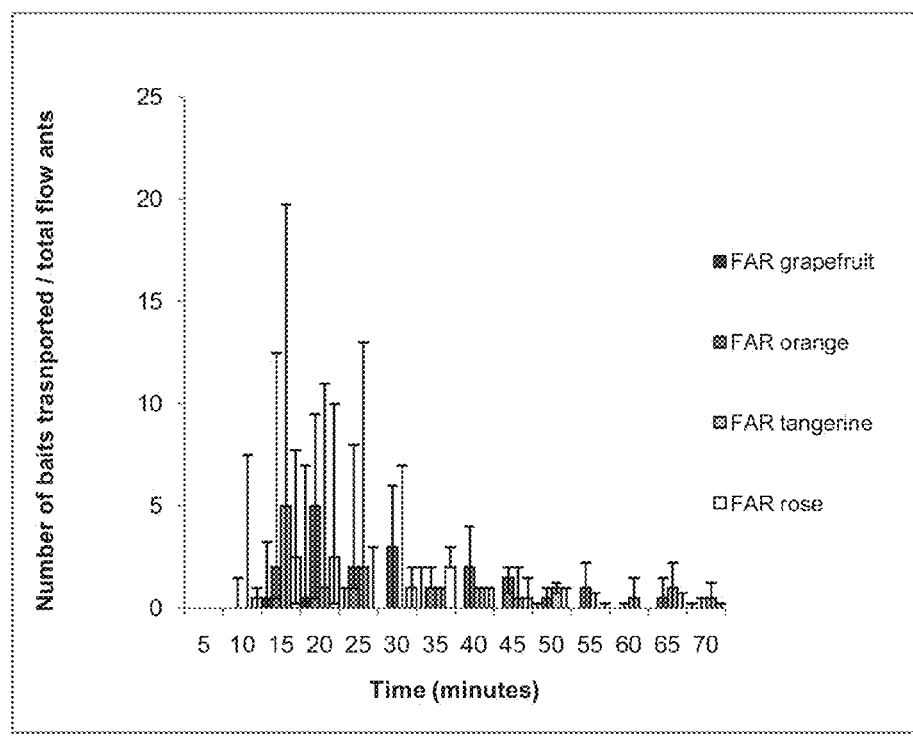
FIG. 13 shows the number of transported grains (as median and as 25 and 75% quartiles) relative to ant total flow, as a function of the time in the assays of Example 11.
Figure 14:
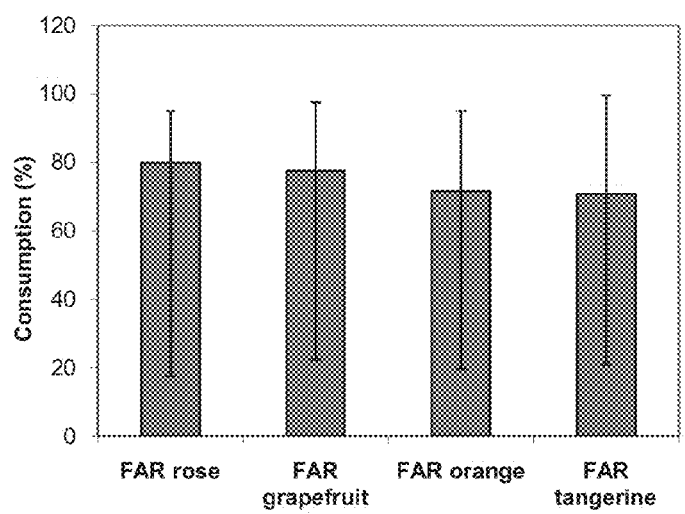
FIG. 14 shows consumption (in percentage, as median and as 25 and 75% quartiles) of the different types of formulations by the 6 colonies in the assays of Example 11.

It was observed that the three formulations with citric extract (grapefruit, orange, and tangerine) were transported for the first time after more than about 20 minutes, while rose FAR was transported after 15 minutes (FIG. 11). However, it was the formulation taking the longest time to be carried to the fungus that serves as food (FIG. 12). Between 70 and 80% of the grains was consumed, with consumption of rose and grapefruit FAR being the highest (FIGS. 13 and 14).

In view of these results, rose extract was chosen as attractant, adding different inert substances which could serve in a formulation with conidia as germination material or medium: corn starch, oats, chitin and confectioner's sugar.

Figure 15:
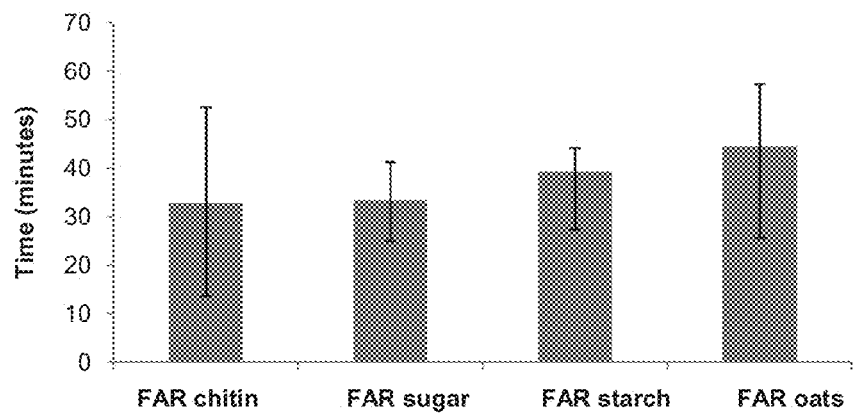
FIG. 15 shows time elapsed until the first grain of formulation was transported by the ants (as median and as 25 and 75% quartiles) in the assays of Example 11.

The formulations were carried for first time in all cases after 30 minutes, with FAR chitin and sugar being carried first (FIG. 15). However, transport to the fungus was fastest for FAR sugar formulation (10 minutes), while consumption was higher for FAR oats, even when transport and placement on the fungus that serves as food took longer (data not shown).

Example 12

Combined Effect of *Escovopsis weberii* and *Purpureocillium lilacinum* in Lab Sub-Colonies Sub-colonies of *A. lundii* were prepared with 15 g of *Leucoagaricus* (including all the ants present in the portion of garden taken) as starting material, and then 100 mid-size to large ants collected from the foraging area were added. After 8 hours the fungus growing chamber, the foraging area and the refuse chamber were connected, and the sub-colonies were used to starting the formulation provision after stabilizing for one week.

3 colonies were used, making 2 sub-colonies from each: one as control (formulations without controlling agent) and one in which formulations prepared as in Example 8 with a concentration of 1.2E+07 for *E. weberii* and 1.2E+08 for *P. lilacinum* (formulations with both controlling agents) were administered. One gram of FG was placed on the fungus the first day, 8 days later FPN was applied and FAV was applied on day 17.

Weight of the fungus was evaluated daily and expressed as a % of the initial weight (15 g).

Figure 16:
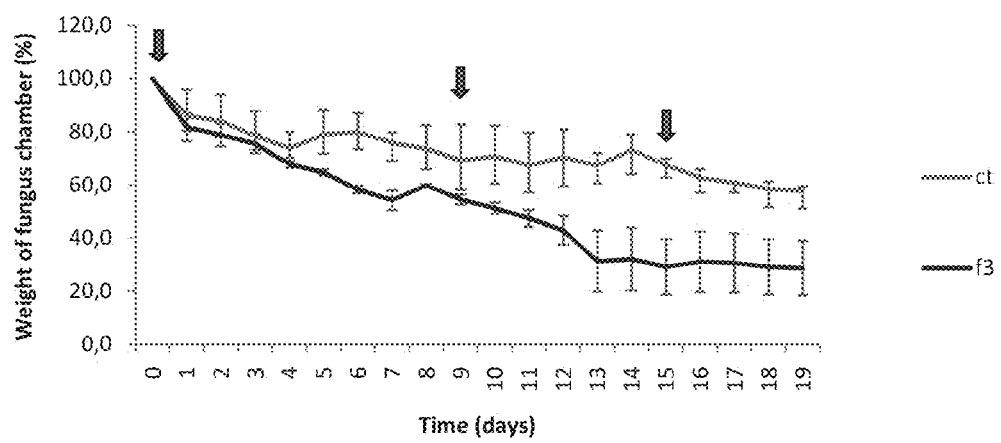
FIG. 16 shows the relative variation in weight (as median and as 25 and 75% quartiles) of *Leucoagaricus* after administration of formulations containing *Escovopsis weberii* and *Purpureocillium lilacinum* of Example 12.

In the colonies treated with the biologic control agents the amount of the fungus that serves as food dropped significantly, as compared with the control (repeated measures ANOVA, F=; p<) and a large number of ants died (FIG. 16). The fact that the curve does not reach zero does not mean that the *Leucoagaricus* garden was not completely dead, but is a result of the fungus not disappearing in all colonies: in some of the colonies the *Leucoagaricus* fungus completely dried out, leaving part of the dead biomass within the fungus growing flask.

Figure 17:
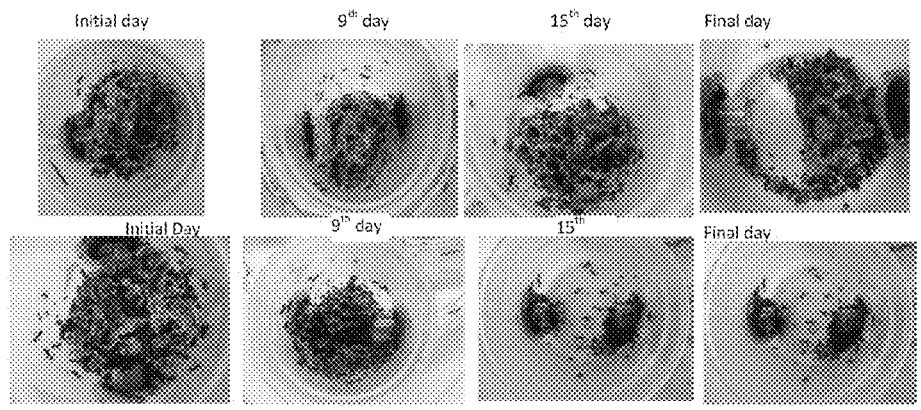
FIG. 17 shows the effect on *Leucoagaricus* cultures of administering formulations containing *Escovopsis weberii* and *Purpureocillium lilacinum* of Example 12.

In FIG. 17 (control pool above, treated with both controlling agents below) shows the colony in which the more drastic effect was recorded during the time in which the treatment was applied.

Example 13

Field Test of *Acromyrmex lundii* Leaf-Cutting Ants Consumption of Formulations without Controlling Agent 8 nests of *Acromyrmex lundii* were used to try each of the formulations FP, FPN, FAV, and FG as in Example 8 but prepared using rice without controlling agent. These formulations were placed in transparent plastic containers with lid. A lateral perforation was practiced on each of these containers as to allow ants to enter and carry away the formulation. Each container had 40 gr of formulation. One container per active trail per nest was placed at the side of the foraging track, about 50 cm away from the nest entrance. In this trial only one formulation was applied to each nest (total of nests used N=32). Once all formulations were in place, all nests were observed as to observe the behavior and flux of carried formulation, measuring the time elapsed until the first formulation grain was carried away (time to $1^{st}$ carrying). 24 h later the containers were collected, and in the case consumption was not 100% of formulation the remnant was weighted, with the purpose of calculating consumption.

Figure 18:
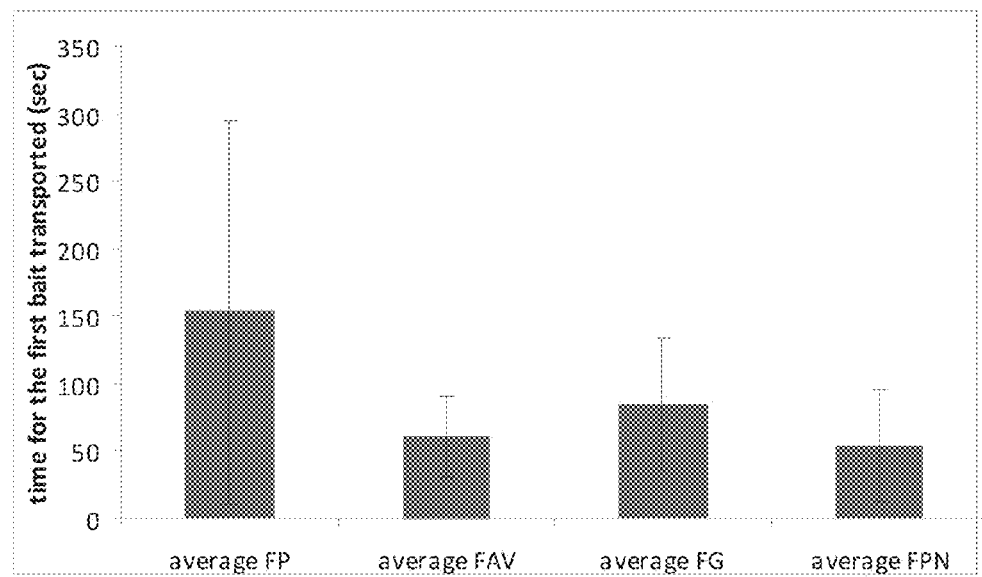
FIG. 18 shows time elapsed until the first grain of formulation was transported (time of 1$^{st}$ carrying) for the formulations of Example 13.
Figure 19:
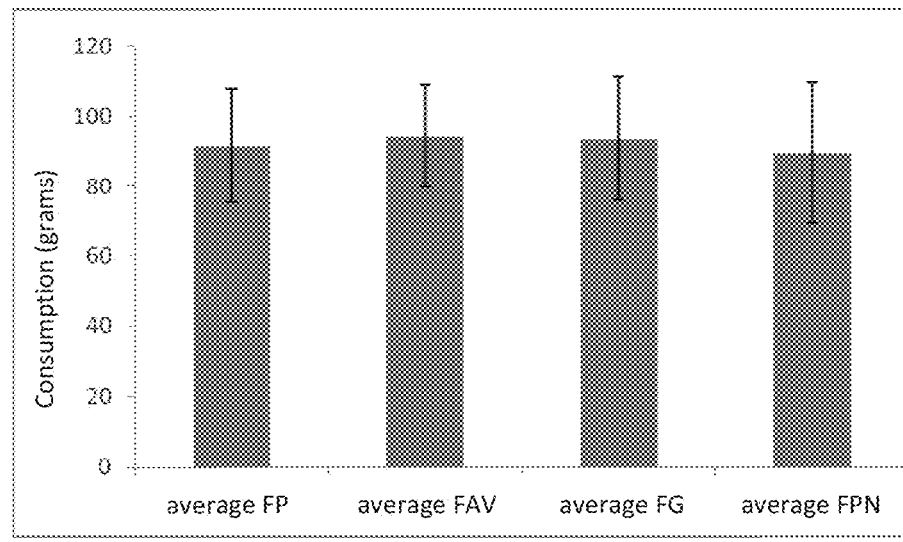
FIG. 19 shows the consumed percentage for each bait formulation administered in Example 13.

Results (FIGS. 18 and 19) show that formulations FAV, FG, and FPN were found by the ants and collected in a very short time (between 53 and 85 seconds). Time to $1^{st}$ carrying was longer for formulation FP (153 sec) but it was also detected relatively soon. The four formulations were highly consumed by the ants, with consumption between 90 and 95%.

Example 14

Consumption of Three Formulations with Different Controlling Agents Administered in Two Cycles of Serial Supplying Three kits of formulations were prepared. The first kit was constituted by formulations FG, FPN, and FAV from Example 8 containing conidia of *Purpureocillium lilacinum*, and the second kit was constituted by the same three formulations but containing a mixture of *Trichoderma harzianum* and *Beauveria bassiana* as controlling agents. Finally, a kit without any controlling agent was prepared as control. 8 nests were used to test each of the three kits (24 nests of *Acromyrmex lundii* in total). Each 8-nest set received a same biological control agent but in three different formulations. For each nest, 40 gr of formulation were applied to each active trail, for a maximum of 3 trails. Application was made at about 50 cm of the entrance. In the first cycle of bait providing, formulations were sequentially provided every 7 days in the following order: FG, FPN, FAV.

Figure 20:
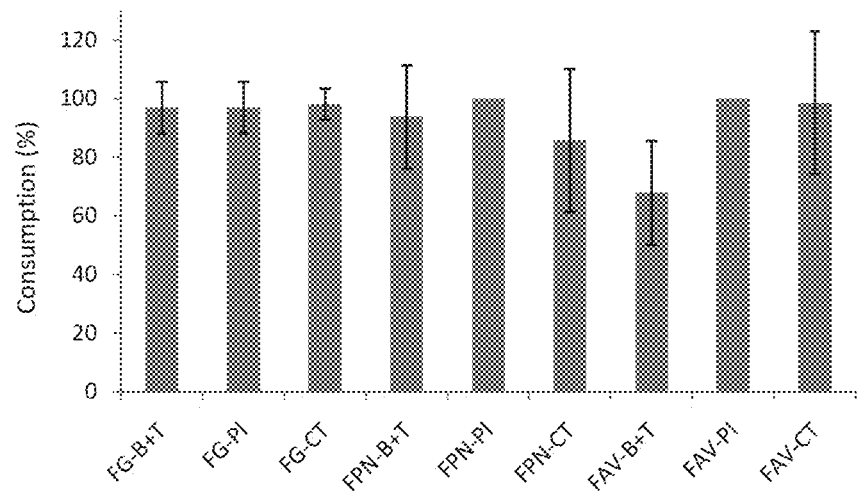
FIG. 20 shows consumption (as a percentage of the total administered) of the different formulation types supplied in the first application cycle of Example 14, grouped by kind of formulation.
Figure 21:
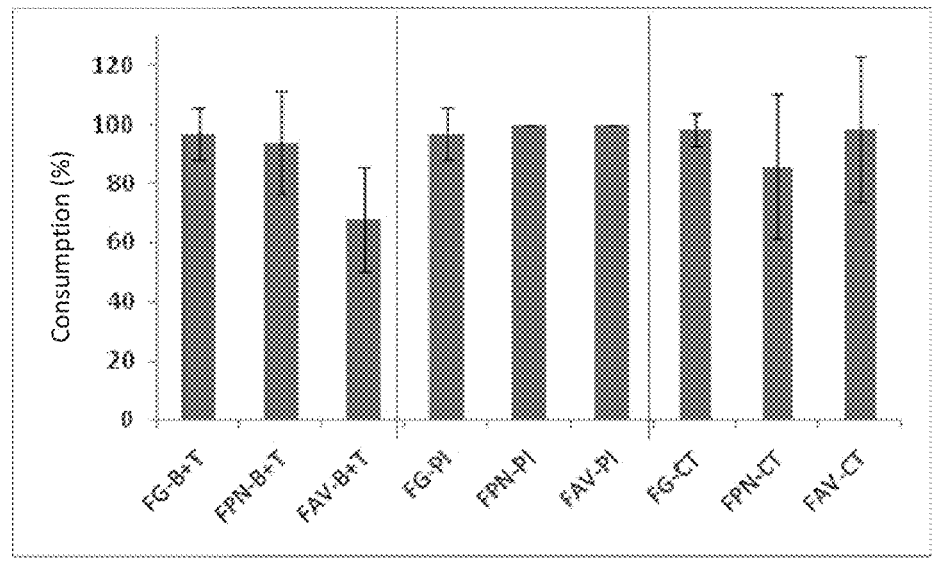
FIG. 21 shows consumption (as a percentage of the total administered) of the different formulation types supplied in the first application cycle of Example 14, grouped by kind of controlling agent.

The results (FIGS. 20 and 21) show that the three formulations containing 1 as well as 2 biological control agents are carried away successfully during three consecutive applications one week apart from each other.

The second cycle of application was performed 12 weeks after application of the first formulation (or 9 weeks after providing the third formulation in the first cycle). The same 24 nests of the first cycle received 40 gr of the same formulations per active trail, for a maximum of 3 trails. Application was done at about 50 cm of the entrance to the nest. Formulations were applied sequentially every 10 days in the following order: FG, FAV, FPN.

Figure 22:
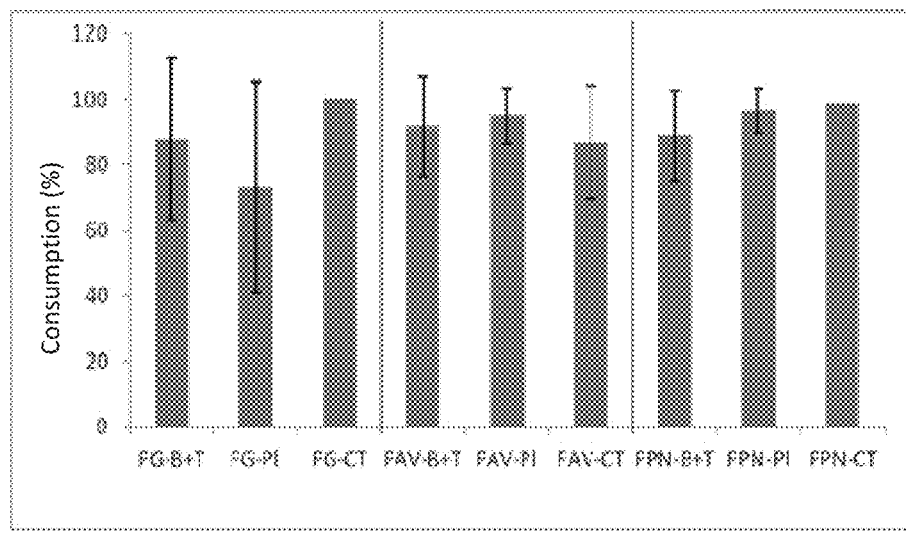
FIG. 22 shows consumption (as a percentage of the total administered) of the different formulation types supplied in the second application cycle of Example 14, grouped by kind of formulation.
Figure 23:
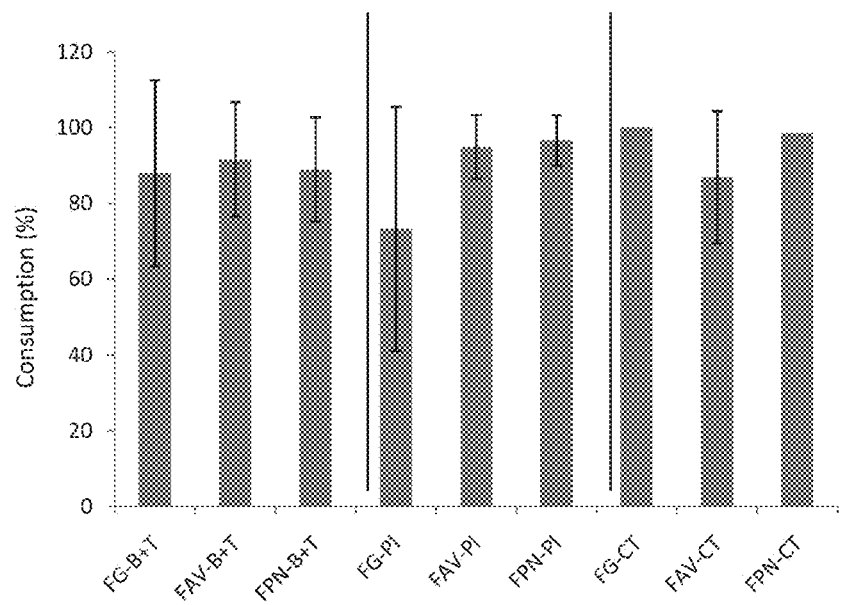
FIG. 23 shows consumption (as a percentage of the total administered) of the different formulation types supplied in the second application cycle of Example 14, grouped by kind of controlling agent.

Again, it was observed that applications of formulations were successful and no delayed rejection was observed because the applied formulations were carried out almost completely (FIGS. 22 and 23).

Figure 24:
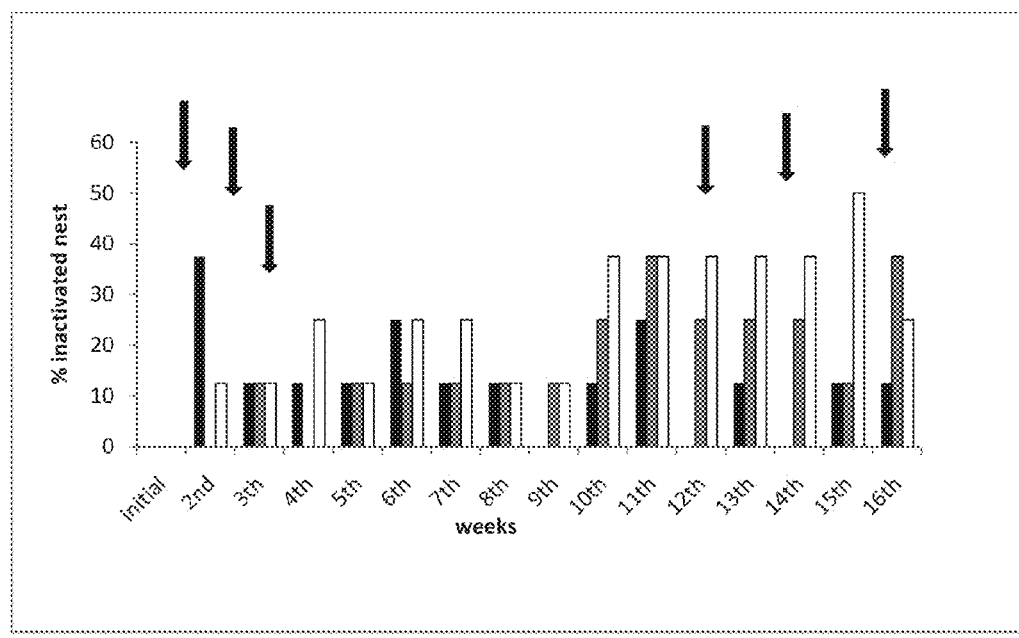
FIG. 24 shows the effect of performing two serial supplying cycles of three formulations of Example 14 on the activity of treated nests, measured as the percentage of nests exhibiting total inactivation.
Figure 25:
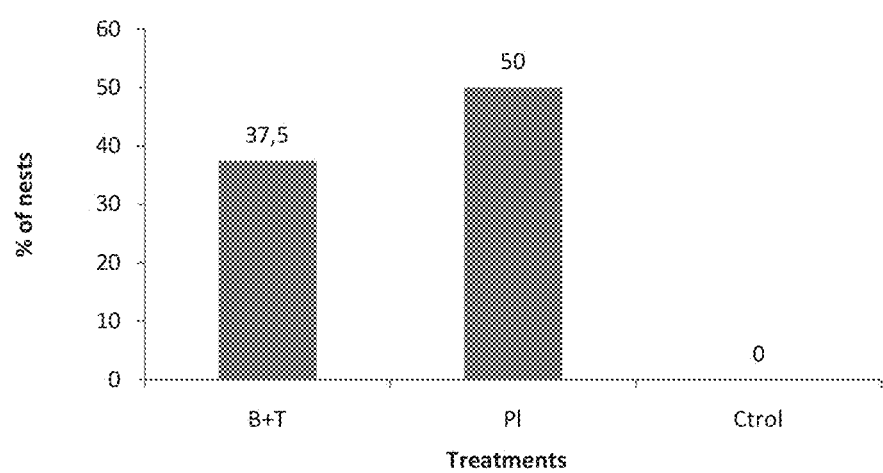
FIG. 25 shows the effect of performing two serial supplying cycles of three formulations of Example 14 on the activity of treated nests, measured as the percentage of nests exhibiting activity lower than 15% of the initial activity for at least 7 consecutive weeks after application of bait formulations.

With the kits applied in the first cycle (FIG. 24, three arrows on the left side) and in the second cycle (FIG. 24, three arrows on the right side) it can be observed a beginning of inactivation, probably due to death, of the treated nests, and a drastic reduction in the activity of the foraging ants of the treated nests (FIG. 25). The very low activity observed for 7 consecutive weeks for the same nests (FIG. 25) is a reliable indicator of the ill health of the colony, which with time and/or a new application cycle, would lead to its death.

The invention claimed is:

1. A kit for the biological control of leaf-cutting ants, comprising at least two granulated bait formulations, each bait formulation comprising:
   a) a biological control agent for the ants, and
   b) a substance or substances selected from one masking substance for the biological control agent, one attractant, and a combination of one masking substance for the biological control agent and one attractant,
   wherein the biological control agent is the same in each bait formulation, wherein all the bait formulations each comprises both *Escovopsis* sp. conidia and *Purpureocillium lilacinum* conidia as the biological control agent, and
   wherein the masking substance for the biological control agent and/or the attractant are different in each bait formulation.

2. The kit of claim 1, wherein the biological control agent is present at a concentration of between $10^3$ and $10^{10}$ viable conidia/gram of formulation.

3. The kit of claim 2, wherein the bait formulations further comprise conidia germination medium.

4. The kit of claim 1, wherein the substance selected is the attractant and the attractant is at least in the form of a coating of the granulated bait formulations.

5. The kit of claim 1, wherein the granulated bait formulations have a grain size between 2.5 and 5 mm.

6. The kit of claim 1, wherein at least one of the bait formulations is in the form of dry pellets.

7. The kit of claim 1, wherein at least one of the bait formulations is in the form of a gelatinous granulated formulation.

8. The kit of claim 1, wherein the substance selected is the attractant and the attractant is selected from the group consisting of plant extracts, plant essential oils, powdered citrus skin, citrus pulp, citrus albedo,—leaves preferred by ants, and rose petals.

9. The kit of claim 1, wherein the bait formulations each differ from one another in at least one additional feature selected from consistency, texture, and grain size.

10. The kit of claim 1, which comprises three bait formulations.

11. The kit of claim 2, wherein the biological control agent is present at a concentration of between $10^8$ and $10^9$ viable conidia/gram of formulation.

12. The kit of claim 3, wherein the conidia germination medium is selected from the group consisting of corn starch, sugar, confectioner's sugar, oats and chitin.

13. The kit of claim 3, wherein the conidia germination medium is different in each formulation.

14. The kit of claim 1, wherein each bait formulation comprises a different strain of the same biological control agent.

* * * * *

UNITED STATES PATENT AND TRADEMARK OFFICE
CERTIFICATE OF CORRECTION

| | |
|---|---|
| PATENT NO. | : 9,578,873 B2 |
| APPLICATION NO. | : 14/351041 |
| DATED | : February 28, 2017 |
| INVENTOR(S) | : Patricia Folgarait et al. |

It is certified that error appears in the above-identified patent and that said Letters Patent is hereby corrected as shown below:

In the Claims

Claim 8, Column 21, Line 7, please delete the "---" between "citrus albedo," and "leaves preferred by".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*